United States Patent [19]

Buchschacher et al.

[11] 4,087,436
[45] May 2, 1978

[54] METHYLATION OF DE-A STEROIDS

[75] Inventors: Paul Buchschacher, Arlesheim; Andor Fürst, Basel; Ludwig Labler, Allschwil; Werner Meier, Bottmingen, all of Switzerland; John William Scott, Upper Montclair, N.J.

[73] Assignee: Hoffmann-La Roche, Inc., Nutley, N.J.

[21] Appl. No.: 589,650

[22] Filed: Jun. 23, 1975

Related U.S. Application Data

[63] Continuation-in-part of Ser. No. 303,917, Nov. 6, 1972, abandoned.

[30] Foreign Application Priority Data

Nov. 12, 1971  Switzerland ............ 16516/71

[51] Int. Cl.$^2$ .............. C07D 261/06; C07D 317/08; C07C 49/54; C07C 49/60
[52] U.S. Cl. .............. 260/307 H; 260/338; 260/340.5 AS; 260/340.9 A; 260/340.7; 260/586 E; 260/586 R
[58] Field of Search .......... 260/307 H, 586 H, 586 E, 260/340.5 AS, 340.9 AS, 340.7, 338

[56] References Cited

U.S. PATENT DOCUMENTS 3,010,974  11/1976  Barkley .............. 260/340.5 AS

FOREIGN PATENT DOCUMENTS 1,196,193  7/1965  Germany ............ 260/340.5 AS

OTHER PUBLICATIONS

J. E. McMurry, Ph.D Thesis, Columbia Univ. N.Y. (1967) pp. 69 and 70.

Primary Examiner—Donald G. Daus
Assistant Examiner—D. B. Springer
Attorney, Agent, or Firm—Samuel L. Welt; George M. Gould

[57] ABSTRACT

Treatment of de-A steroids with a methylation agent at extremely low temperatures, i.e., below −50° C. produces corresponding 10$\beta$-methyl−$\Delta^{9(11)}$-deA steroids with a high 10$\beta$ to 10$\alpha$ isomer ratio. A number of the product 10$\beta$-methyl-$\Delta^{9(11)}$-deA steroids are novel compounds. They are useful as intermediates in the synthesis of known medicinally valuable steroids.

8 Claims, No Drawings

METHYLATION OF DE-A STEROIDS

RELATED APPLICATIONS

This application is a continuation-in-part of applicants' co-pending application Ser. No. 303,917 filed Nov. 6, 1972, now abandoned.

BACKGROUND OF THE INVENTION

German Patent No. 1,196,193 dated July 8, 1965 discloses the alkylation of a 17β-acyloxy-3,5-diketo-4,5-seco-19-nor-Δ$^9$-androstene, which is selectively ketalized in the 3-position, by means of a lower molecular weight alkylation agent in the presence of an alkali metal tert.-alcoholate to yield in a stereospecific reaction only the corresponding 10β-compound.

A subsequent study [J. E. McMurry, Ph.D. Thesis, Columbia University, New York, (1967)] was unable to confirm this statement. On the contrary, under various reaction conditions, including those given in the aforementioned Patent Specification, there was obtained a mixture of 10β:10α-compounds in the proportion 2:1.

DESCRIPTION OF THE INVENTION

The present invention relates to an improved process for the preparation of 10β-methyl-Δ$^{9(11)}$-deA steroids. In this process a deA-steroid of the general formula

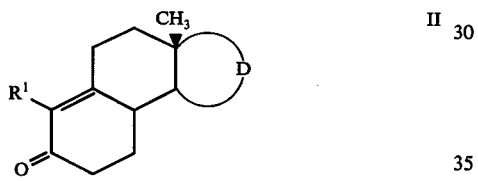

II wherein R$^1$ is a substituent conventionally utilized for the synthesis of the steroid-A-ring and D is the remainder of a 5- or 6-membered steroid-D-ring, is treated at a temperture below −50° C. with a methylation agent so as to produce the corresponding 10β-methyl-Δ$^{9(11)}$-deA steroids of the following general formula

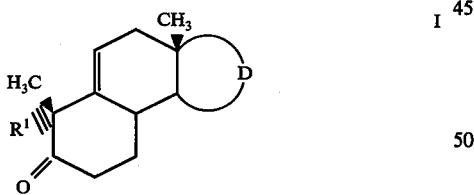

I wherein R$^1$ and D are as above.

It has unexpectedly been found that when the aforesaid process is carried out at the indicated low temperatures that the 10β:10α-proportion in the resulting product of formula I is 4:1 or even greater. Most preferably the process of this invention is conducted at a temperature in the range of from about −70° C. to about −110° C.

As the methylation agent there can be used methylation agents which are known to be suitable for C-alkylation; for example, methyl halides, especially methyl iodide, in the presence of a base such as sodium hydride, sodium amide or potassium tert-butylate. Examples of other methylation agents are dimethyl sulfate and methyl esters of sulfonic acids.

As solvents for the methylation there can be used, in particular, ethers such as ethyleneglycol-dimethyl ether, ethyleneglycol-diethyl ether, diethyleneglycol-dimethyl ether, diethyleneglycol-diethyl ether and tetrahydrofuran.

Preferred deA-steroid starting materials of formula II are those in which D represents a grouping of the formula

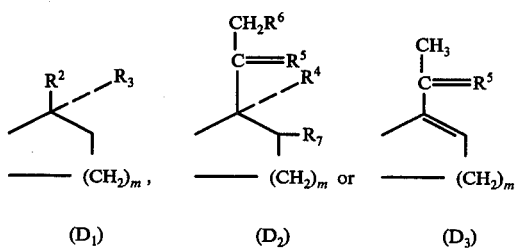

wherein m is 1 or 2, R$^2$ is a free, esterified or etherified hydroxy group, R$^3$ is a hydrogen atom or a lower alkyl or lower alkynyl group, or R$^2$ and R$^3$ together are a ketal group, an ethylidene group, a 1-(lower alkanoyloxy)-ethylidene group or a group of the formula

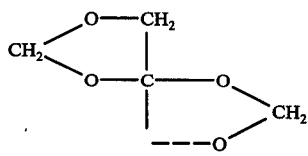

R$^4$ is a hydrogen atom or a hydroxy group and R$^5$ is an oxo group, a ketal group or (hydrogen and hydroxy), (hydrogen and esterified hydroxy) or (hydrogen and etherified hydroxy), R$^6$ is a hydrogen atom or a hydroxy, esterified hydroxy or etherified hydroxy group, R$^4$ and R$^6$ together are lower alkylidenedioxy in the case where R$^5$ represents an oxo group and R$^7$ is a hydrogen atom or a methyl group.

Preferred values for R$^1$ in formulae I and II hereinbefore are ketalized 3-oxobutyl, 3-chloro-2-butenyl, 3-methyl-3-butenyl, 3-(lower alkoxy)-2-butenyl, 3-(lower alkoxy)-3-butenyl, 3-hydroxy-butyl (and esters and ethers thereof), 2-cyanoethyl, 2-carboxyethyl, 2-(lower alkoxycarbonyl)-ethyl or a grouping of the formula

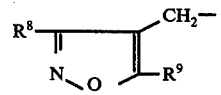

wherein R$^8$ and R$^9$ each is a hydrogen atom or an identical lower alkyl group provided that at least one of R$^8$ or R$^9$ is a lower alkyl group.

An esterified hydroxy group is preferably a lower alkanoyloxy group such as acetoxy over an aroyloxy group such as benzoyloxy. Etherified hydroxy groups are preferably lower alkoxy groups such as tertbutoxy, (lower alkoxy)-(lower alkoxy) groups such as methoxymethoxy as well as benzyloxy and tetrahydropyranyloxy. Groups prefixed by the expression "lower" are those which contain up to 6 carbon atoms. Examples of ketal groups are lower alkylene ketal groups such as ethylenedioxy, 2,3-butylenedioxy and propylene dioxy, 2-ethyl-, 2-phenyl-, 2,2-diethyl- or 2,2-diphenyl-propylenedioxy, arylene ketal groups such as 1,2-phenylenedioxy, alkylated 1,2-phenylenedioxy and 2,3-naphthylenedoxy and di(lower) alkyl) ketal groups such as dimethoxy and diethoxy. Such ketal groups can be split off in a manner known per se after the methylation has been effected, whereby there are obtained, for example, 10$\beta$-methyl-$\Delta^{9(11)}$-deA-steroids of formula I in which D represents a grouping of formula $D_1$ hereinbefore and $R_2$ and $R_3$ therein together represent an oxo group.

10$\beta$-Methyl-$\Delta^{9(11)}$-deA-steroids of formula I in which $R^1$ and D have the significance given earlier with the exception of those in which m is 1, $R^1$ is a ketalized 3-oxobutyl or 3-chloro-2-butenyl group, $R^2$ is an esterified hydroxy group and $R^3$ is a hydrogen atom are novel and it will be appreciated that they form part of this invention. The manufacture of these novel 10$\beta$-methyl-$\Delta^{9(11)}$-deA-steroids from the corresponding deA-steroids of formula II represents a preferred embodiment of the present invention.

A preferred process embodiment of the present invention is obtained when m is 1; $R^2$ is acetoxy, tert-butoxy, methoxymethoxy, benzyloxy, or tetrahydropyranyloxy; $R^3$ is a hydrogen atom or a methyl or ethynyl group; or $R^2$ and $R^3$ taken together are lower alkylenedioxy or phenylenedioxy; $R^4$ is a hydrogen atom; $R^5$ is a lower alkylenedioxy or lower alkanoyloxy group; and $R^6$ and $R^7$ each is a hydrogen atom.

The 10$\beta$-methyl-$\Delta^{9(11)}$-deA-steroids of formula I are valuable intermediates in the synthesis of medicinally valuable steroids. Their transformation into such steroids can be carried out according to known methods. For example, by use of procedures described in U.S. Pat. Nos. 3,544,598 and 3,544,600 both issued Dec. 1, 1970 or in U.S. Patent applications Ser. No. 778,314 filed Nov. 22, 1968, now U.S. Pat. No. 3,707,061 and Ser. No. 845,546, filed July 28, 1969, now U.S. Pat. 2,692,803.

The following Examples illustrate the present invention.

EXAMPLE 1

A solution of 3.85 g. of 17$\beta$-tertbutoxy-19-(3,5-dimethyl-4-isoxazolyl)-deA-androst-9-en-5-one and a drop of tertbutanol in 120 ml. of tetrahydrofuran was flushed with nitrogen. Thereafter, 480 mg. of a 50% suspension of sodium hydride in mineral oil were added and the resulting suspension was heated for 18 hours under moderate reflux. The so-obtained light-brown solution was cooled in a dry-ice/acetone bath (bath temperature −78° C to −80° C., internal temperature −73° C. to −75° C) and treated in the course of 2 minutes with 2.5 ml. of methyl iodide. The solution was stirred for 8 hours at −75° C., subsequently treated at this temperature with a small amount of water, diluted with benzene and the organic phase separated. The latter was washed with sodium chloride solution and dried over sodium sulfate. Gas-chromatographic analysis of the residue remaining after concentration showed, in addition to a trace of unknown materials 82.2% of 10$\beta$-methyl compound and 17.8% of 10$\alpha$-methyl compound. The residue, 4.53 g. of a light-yellow oil, was chromatographed on 500 g. of silicagel with hexane/ether (9:1). There could thereby be eluted 3.116 g. of 17$\beta$-tertbutoxy-10$\alpha$-[(3,5-dimethyl-4-isoxazolyl)-methyl]-deA-androst-9(11)-en-5-one. Recrystallization thereof from 10–12 ml. of hexane yielded 2.6 g. of fine, white prisms of melting point 105°–107° C; $[\alpha]_D^{25}$ = +17.4° (c = 1.08 in chloroform).

The foregoing reaction was repeated using monomethylglycol as the solvent and a reaction time of 6 hours. Gas chromatograph showed 0.2% of unknown material, 80.3% of 10$\beta$-methyl compound and 19.5% of 10$\alpha$-methyl compound.

EXAMPLE 2

To a solution of 3.99 g. of 20$\beta$-acetoxy-19-(3,5-dimethyl-4-isoxazolyl)-deA-pregn-9-en-5-one in 120 ml. of ethylene glycol dimethyl ether were added 530 mg. of a 50% suspension of sodium hydride in mineral oil and the mixture was boiled at reflux for 18 hours with continuous gassification with argon. The light-brown solution was then brought to an internal temperature of −72° C. to −75° C. by means of a dry-ice/acetone bath and treated dropwise during 2 minutes with 2.5 ml. of methyl iodide. After stirring for 6.5 hours at −72° C. to −75° C., 20 ml. of water were added and the cooling bath was removed. The solution was then taken up in benzene and the aqueous phase separated. The benzene solution was washed with aqueous sodium chloride solution and then dried over anhydrous sodium sulfate. After filtration, the filtrate was concentrated in a water-jet vacuum, the residue diluted with 25 ml. of pyridine and 13 ml. of acetic anhydride were added thereto. After leaving at room temperature for 18 hours the solution was treated first with ice-water and then with ether. The ethereal phase was separated, washed first with 1N hydrochloric acid, then with saturated sodium hydrogen carbonate solution and finally with water. After drying over anhydrous sodium sulfate and filtration under suction, the filtrate was concentrated to dryness. The residue (4.3g.), which consisted of a mixture of 10$\beta$:10$\alpha$-methyl compounds in the proportion 78:22 according to gas chromatography, was chromatographed on a column of 500 g. of silica gel in hexane. By elution with a mixture consisting of 7 parts of hexane and 3 parts of ether there were obtained 2.7 g. of an uniform crude product as an apolar fraction. Recrystallization thereof from methylene chloride/ether gave 2.3 g. of pure 20$\beta$-acetoxy-10$\alpha$-[3,5-dimethyl-4-isoxazolyl)-methyl]-deA-pregn-9(11)-en-5-one of melting point 136°–137.5° C; $[\alpha]_D$ = +20° (c = 0.1 in dioxane).

EXAMPLE 3

To a solution of 2 g. of 3,3-ethylenedioxy-17$\beta$-tertbutoxy-4,5-seco-19-nor-androst-9-en-5-one in 60 ml. of tetrahydrofuran were added 295 mg. of a 50% suspension of sodium hydride in mineral oil. The mixture was heated at reflux for 18 hours under argon gassification. The light-brown solution was then brought to an internal temperature of −72° C. to −75° C and treated dropwise during 2 minutes with 1.25 ml. of methyl iodide. After stirring for 6.5 hours at −72° C. to −75° C., 10 ml. of water were added thereto. The temperature was raised to 0° C. and then the mixture was diluted with 200 ml. of water and extracted with ether. The combined organic phases were washed with water and brine, dried over sodium sulfate, filtered and the filtrate evaporated in a vacuum. The residue (2.2 g.) contained, according to gas chromatography, apart from starting material 61.3% of a mixture of 10$\beta$-methyl and 10$\alpha$-methyl compounds (proportion by weight 4.67:1).

The residue was stirred for 4 hours at 60° C. in 30 ml. of glacial acetic acid and 5 ml. of water. The mixture was diluted with water and extracted with ether. The combined extracts were washed successively with saturated sodium bicarbonate solution and water, dried over anhydrous sodium sulfate, filtered and the filtrate evaporated in a vacuum. The brown oily residue (1.85 g.) was chromatographed on 190 g. of silicagel in hexane/ether (98:2). From the purest fractions there were obtained 460 mg. (25% of theory) or oil 17β-tertbutoxy-4,5-seco-androst-9(11)-ene-3,5-dione; $[\alpha]_D = +38°$ (c = 0.1 in dioxan).

EXAMPLE 4

To a solution of 4.3 g. of 3,3-orthophenylenedioxy-17β-tertbutoxy-4,5-seco-19nor-androst-9-en-5-one in 100 ml. of tetrahydrofuran were added 500 mg. of a 50% suspension of sodium hydride in mineral oil. The mixture was boiled at reflux for 18 hours under argon gassification, subsequently cooled to $-72°$ C. and treated with 3 ml. of methyl iodide. Stirring for 6.5 hours at $-72°$ C. to $-75°$ C. and working up in the manner described in the first paragraph of Example 3 gave a product which contained in addition to starting material 73% of a mixture of 10β-methyl and 10α-methyl compounds (proportion by weight 4.5:1). Chromatography on silica gel using hexane/ether (80:20) gave pure 3,3-orthophenylenedioxy-17β-tertbutoxy-4,5-seco-androst-9(11)-en-5-one; $[\alpha]_D = +25°$ (c = 0.1 in dioxan).

EXAMPLE 5

A mixture of 2.40 g. (6.0 mmoles) of 17β-tertbutoxy-10-[(3,5-dimethyl-4-isoxazolyl)methyl]-deA-androst-9(11)-en-5-one, 500 mg. of p-toluenesulfonic acid monohydrate, 20 ml. of ethylene glycol, and 100 ml. of benzene was degassed, placed under $N_2$, and heated at reflux, with azeotropic removal of $H_2O$, for 20 hours. The solution was cooled, washed with saturated NaHCO$_3$ solution and $H_2O$ and dried ($Na_2SO_4$). Solvent removal gave a white foam: TLC (1:1 benzene-ethyl acetate) $R_f$ 0.56 and 0.31 (ca. 1:1). The crude ketals were taken up in 100 ml. of 5% ethanolic KOH. To this solution was added 500 mg. of 5% palladium on carbon catalyst and the resulting suspension was hydrogenated at atmospheric pressure and room temperature. After 45 minutes, the uptake of $H_2$ (180 ml) had ceased. The catalyst was removed by filtration and washed with fresh ethanol. The colorless filtrate was stripped of solvent until a residue of ca. 30 ml. remained. To this solution of the vinylgous amides was added 100 ml. of 20% KOH solution and the resulting mixture was degassed, placed under $N_2$, and heated at reflux for 18 hours. The two-phase solution was cooled and extracted with benzene. The benzene solutions were washed with saturated brine and dried ($Na_2SO_4$). Solvent removal gave a light yellow resin: TLC (1:1 benzene-ethyl acetate) $R_f$ 0.58 and 0.30 (ca. 1:1). To a solution of the keto diketals in 100 ml. of methanol was added 10 ml. of 3N HCl and the resulting solution was heated at reflux under $N_2$ for 3.0 hours. The solution was cooled, poured into $H_2O$-brine, and extracted with benzene. The benzene solutions were washed with $H_2O$ and dried ($Na_2SO_4$). Solvent removal gave a yellow resin: TLC (1:1 benzene-ethyl acetate) $R_f$ 0.56 and 0.29 (ca. 1:2). To a solution of the crude steroid mixture in 50 ml. of benzene was added 0.5 g. of p-toluenesulfonic acid monohydrate and the resulting mixture was heated at reflux for 1.0 hour. Another 0.5 g. of acid was added and heating was continued for an additional hour. The solution was cooled, washed with saturated NaHCO$_3$ solution and $H_2O$ and dried ($Na_2SO_4$). Solvent removal gave 1.50 g. of red-brown resin: TLC (1:1 benzene-ethyl acetate) $R_f$ 0.28. The material was chromatographed on 100 g. of E. Merck 0.05–0.2 mm silica gel with 7:3 hexane-ethyl acetate to give 1.077 g. of yellowish solid. Crystallization from $CH_2Cl_2$-isopropyl ether gave 916 mg. (53%) of 17β-hydroxy-androsta-4,9(11)-dien-3-one as clear, slightly-yellow prisms: m.p. 152.5°–156°, mmp with an authentic sample 153°–156.5° C $[\alpha]_D^{25}$ +92.4° (c 1.12, CHCl$_3$); uv max ($C_2H_5OH$)238 nm ($\epsilon$ = 17,100) [reported uv max 238 nm ($\epsilon$ = 16,800)]. The ir and nmr spectra of this material were the same as those of authentic product.

EXAMPLE 6

A solution of 12.7 g. of 17β-t-butoxy:4,5-secoestr-9-en-3,5-dione 3-(2,2-dimethyltrimethylene acetal) and 2 drops of t-butyl alcohol in 130 ml. of dry glyme was placed under argon. To the flask was added 1.72 g. of 50% sodium hydride in mineral oil and the resulting suspension was heated at a gentle reflux for 18 hours. The light brown solution was cooled to $-70°$ as 10.7 ml. of methyl iodide was added via syringe over 5 min. The solution was stirred at $-70°$ for 90 minutes, quenched with 60 ml. of water at this temperature, and the flask allowed to reach 0°. The reaction mixture was poured into 1.5 l. of water and the products extracted with ether. The etheral extract was washed with water and saturated brine, dried with sodium sulfate and evaporated to dryness. Gas chromotography showed the crude product to consist of two major compounds in a ratio of 4:1. The light brown resin was chromatographed on 400 g. of silica gel. Elution with n-hexane/ether 9:1 afforded 6.6 g. of an oil which was shown to be homogeneous by thin layer chromatography. This material was dissolved in n-hexane and cooled to give 0.95 g. of crude 17β-t-butoxy-4,5-seco-10α-androst-9(11)-en-3,5-dione 3-(2,2-dimethyltrimethylene acetal as white crystals, m.p. 114°–117°. Recrystallization from n-pentane gave analytically pure material: m.p. 123° and 135°; $[\alpha]_D^{25}$ + 37° (c = 0.1, dioxane). The hexane mother liquor was stripped of solvent and the solid residue was crystallized from methanol to give 2.85 g. of analytically pure 17β-t-butoxy-4,5-secoandrost-9(11)-en-3,5-dione 3-(2,2-dimethyltrimethylene acetal) as white needles: m.p. 92°–93°; $[\alpha]_D^{25}$ + 32° (c = 0.1, dioxane).

EXAMPLE 7

Four solutions of the C(10)-anion of 17β-t-butoxy-4,5-secoester-9-en-3,5-dione-3-(2,2-dimethyltrimethylene acetal) were prepared as follows:

To a solution of 2 g. of 17β-t-butoxy-4,5-secoestr-9-en-3,5-dione 3-(2,2-dimethyltrimethylene acetal) in 5 ml. of dry hexamethyl-phosphoramide was added 0.27 g. of 50% sodium hydride in mineral oil. The suspension was heated at 80° for 16 hours in an argon atmosphere. The yellow solution was cooled to 0°, and 32 ml. of dry tetrahydrofuran was added.

These solutions were methylated at temperatures described in Table 1 below by adding 1.72 ml. of methyl iodide and stirring for 4 hours. After this time the solutions were quenched with water at this temperature, and the products were extracted with ether. Gas chromatography of the raw materials showed the results as indicated in Table 1.

TABLE 1

| Run | Temperature | % 10β-CH₃* | % 10α-CH₃* | Ratio 10β/10α |
|---|---|---|---|---|
| 1 | 0° | 54.9 | 31.4 | 1.75 |
| 2 | −25° | 55.8 | 25.2 | 2.2 |
| 3 | −70° | 63.9 | 18.0 | 3.6 |
| 4 | −100° | 81.7 | 12.8 | 6.4 |

*Percent yields are relative yields. In cases where the total is not 100%, the difference represents starting material or by-products.

EXAMPLE 8

Solutions from 1 g. of 17β-t-butoxy-4,5-secoestr-9-en-3,5-dione 3-(2,2-dimethyltrimethylene acetal), 2.5 ml. of dry hexamethylphosphoramide and 0.17 g. of 50% sodium hydride in mineral oil, prepared as described in Example 7, were cooled to 0° and diluted with 17 ml. of a single solvent or of a solvent mixture. After cooling to the desired temperature these solutions were methylated by using 1 ml. of methyl iodide and worked up as previously described. Solvents used, methylation conditions and results of the gas chromatographic analysis of the methylation mixtures are presented in Table 2 following.

TABLE 2

| Run | Solvent | Methylation Conditions | % 10β-CH₃ | % 10α-CH₃ | Ratio 10β/10α |
|---|---|---|---|---|---|
| 5 | Trimethylene oxide | −85°/3 h | 86.2 | 11.2 | 7.7 |
| 6 | Pyridine/Tetrahydrofuran 1:6 | −105°/3 h | 82.6 | 15.1 | 5.4 |
| 7 | Dimethoxy methane | −105°/1 h | 67.8 | 17.5 | 3.9 |
| 8 | Isopropyl amine | −100°/1 h | 74.8 | 14.0 | 5.3 |
| 9 | Isopropyl amine | −75°/1 h | 69.5 | 17.5 | 3.9 |
| 10 | Methoxyethyl amine | −75°/3 h | 79.4 | 17.6 | 4.5 |
| 11 | Ethyl amine | −75°/3 h | 72.3 | 17.4 | 4.2 |
| 12 | t-butyl alcohol/n-pentane 1:6 | −70°/1 h | 75.7 | 20.3 | 3.7 |
| 13 | Acetonitril/n-pentane 1:6 | −80°/1 h | 74.4 | 20.9 | 3.6 |
| 14 | Pyridine/isopropyl chloride 1:6 | −120°/6 h | 80.1 | 12.8 | 6.3 |
| 15 | Tetrahydrothiophene | −90°/3 h | 58.6 | 10.1 | 5.8 |
| 16 | Dimethylformamide diethyl acetal | −75°/3 h | 71.7 | 18.6 | 3.9 |
| 17 | Dimethylacetamide/tetrahydrofuran 1:6 | −100°/1 h | 83.1 | 15.7 | 5.3 |
| 18 | Ethyl butyrate | −95°/1 h | 76.8 | 17.6 | 4.3 |
| 19 | Pyrrolidine | −75°/1 h | 70.9 | 17.8 | 4.0 |
| 20 | Isopropyl chloride | −105°/1 h | 87.1 | 10.8 | 8.0 |
| 21 | s-Butyl chloride | −125°/3 h | 86.1 | 13.5 | 6.4 |

*Percent yields are relative yields. In runs 5–16 the difference of the total of 10β and 10α to 100% represents starting material or by-products. In runs 17–21 the gas chromatographic analysis was performed after separation of the C(10)-methyl compounds from by-products and starting material. For this separation preparative thin layer chromatography was used.

EXAMPLE 9

To a solution of 2 g. of 17β-t-butoxy-4,5-secoestr-9-en-3,5-dione 3-(2,2-dimethyltrimethyl acetal) in 20 ml. of dry dimethylformamide was added 0.27 g. of 50% sodium hydride in mineral oil. The resulting suspension was heated for 16 hours at 80° in an argon atmosphere. The light brown solution was cooled to −50° at 1.72 ml. of methyl iodide was added over 2 minutes. The solution was stirred at −50° for 3 hours, quenched with water at this temperature, and worked up with ether. Gas chromatography showed the crude product to contain 46.7 % of 10β-methyl compound and 11.5% of 10α-methyl compound; ratio 10β/10α-4.05.

EXAMPLE 10

A solution of 7.97 g. of 17β-t-butoxy-4,5-secoestr-9-en-3,5-dione 3-(0-phenylene acetal) and 1 drop of t-butyl alcohol in 78 ml. of dry glyme was treated with 1 g. of sodium hydride in mineral oil. The suspension was heated at a gentle reflux for 18 hours under argon. The solution was cooled to −70° and 6.75 ml. of methyl iodide was added dropwise within 5 minutes. The solution was stirred at −70°, quenched with 80 ml. of water at this temperature, and the products extracted with ether. The ethereal extract was washed with saturated brine, dried with sodium sulfate and evaporated to dryness. Gas chromatography showed the crude product to consist of two major compounds in a ratio of 4.8:1. Chromatography of this product mixture on 220 g. of silica gel with n-hexane/ether 9:1 gave 4.9 g. of a white resin which crystallized after during some methanol. The solid that separated was recrystallized several times from methanol to give 2.33 g. of analytically pure 17β-t-butoxy-4,5-secoandrost-9(11)-en-3,5-dione 3-(0-phenylene acetal) as white needles: m.p. 88°–89°; $[\alpha]_D^{25} + 40°$ (c = 0.1, dioxane).

To a solution of 2 g. of 17β-t-butoxy-4,5-secoestr-9-en-3,5-dione 3-(0-phenylene acetal) in 5 ml. of dry hexamethylphosphoramide was added 0.33 g. of 50% sodium hydride in mineral oil. The suspension was heated at 80° for 18 hours in an argon atmosphere. The solution was cooled to 0°, and 34 ml. of isopropyl chloride was added. The mixture was cooled to −115° as a 2 ml. of methyl iodide was added over 2 min. After stirring for 3 hours at −115° the reaction mixture was quenched with 10 ml of water at this temperature. The cooling water was removed, and the mixture was diluted with water. Working up with ether yielded 2.2 g. of a brown resin. From an aliquot part of the raw product the mixture of both C(10)-methyl compounds was separated from starting material and by-products by preparative thin layer chromatography using hexane/ether 2:1 as solvent system. Gas chromatography showed the isolated material to consist of 86.6% of 10β-methyl compound and 13.4of 10α-methyl compound; ratio 10β/10α= 6.45.

EXAMPLE 11

1 g. of 3,3-(2-butenylendioxy)-17β-t-butoxy-4,5-secoestr-9-en-5-one was added to a suspension of 84 mg. of sodium hydride in 2.5 ml. of dry hexamethylphosphoramide. This mixture was stirred at room temperature for 2 hours under argon, cooled to 0°, and 17 ml. of isobutylchloride/pyridine 6:1 was added, and the stirring continued for 3 hours at the same temperature. The reaction mixture was quenched with 10 ml. of water and allowed to reach 0°. It was then diluted with waer, and the products extracted with ether. The etheral extract was washed with saturated brine, dried over sodium sulfate and stripped of solvent. Gas chromatography showed the crude product to contain two major compounds in a ratio of 3.85:1.It was chromatographed on 60 g. of silica gel. Elution with n-hexane/ether 9:1 afforded 0.83 g. of the pure mixture of both C(10)-methyl compounds. This mixture was dissolved in n-pentane and cooled to give 0.29 g. of 3,3-(2-butenylenedioxy-17β-t-butoxy-4,5-secoandrost-9(11)-en-5-one. Recrystallization from n-pentane gave an analytical sample was white needles: m.p. 96°–97°; [α]$_D^{25}$ + 48° (c = 0.5, chloroform). The n-pentane mother liquor was evaporated, and the residue was chromatographed on 55 g. of silica gel. Elution with n-hexane/ether 49:1 afforded int he most polar fractions some pure crystalline 3,3-(2-butenylenedioxy-17β-t-butoxy-4,5-seco-10K -androst-9(11)-en-5-one. Recrystallization from isopropyl ether gave an analytical sample as white needles: m.p. 108°–109°; [α]$_D^{25}$ + 27° (c = 0.25, chloroform).

We claim:

1. In a process wherein a de A-steroid of the formula

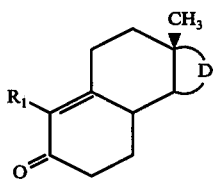

wherein R' is a ketalized 3-oxobutyl; 3-chloro-2-butenyl; 3-methyl-3-butenyl; 3-(lower alkoxy)-2-butenyl; 3-(lower alkoxy)-3-butenyl; 3-hydroxy butyl; 3-esterified-hydroxy-butyl; 3-etherified-hydroxy-butyl; 2-cyanoethyl; 2-carboxyethyl; 2-(lower alkoxy-carbonyl)-ethyl or of the formula

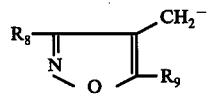

wherein $R^8$ and $R^9$ each is hydrogen or identical lower alkyl provided that at least one of $R^8$ or $R^9$ is lower alkyl; and D is of the formula

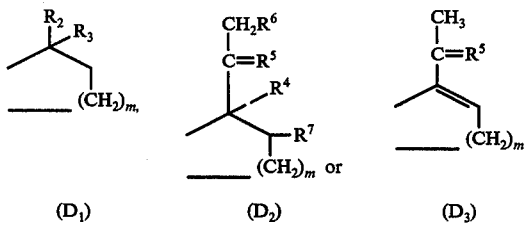

wherein m is 1 or 2; $R^2$ is free, esterified or etherfied hydroxy; $R^3$ is hydrogen, lower alkyl or lower alkynyl; $R^2$ and $R^3$ together are a ketal, an ethylidene group, a 1-(lower alkanoyloxy)-ethylidene group or a group of the formula

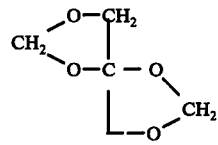

$R^4$ is hydrogen or hydroxy, $R^5$ is oxo, a ketal, (hydrogen and hydroxy), hydrogen and esterified hydroxy) or (hydrogen and etherified hydroxy); $R^6$ is hydrogen, hydroxy, esterified hydroxy or etherified hydroxy; $R^4$ and $R^6$ together are lower alkylenedioxy in the case where $R^5$ is oxo; and $R^7$ is hydrogen or methyl, is treated with a methylation agent in the presence of a base selected from sodium hydride, sodium amide and potassium tert.-butyl alcoholate so as to produce a mixture of compounds of the formula

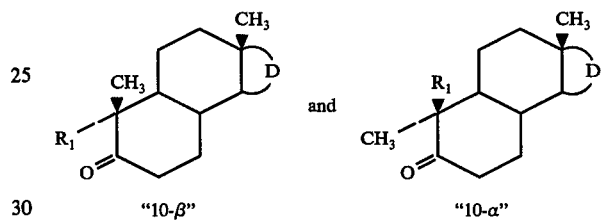

the improvement which comprises the step of utilizing a methylating agent selected from methyl iodide and methyl bromide and a reaction temperature in the range of from about −50° C. to about −125° C. so as to obtain an isomeric ratio of β to 10α of at least 3.6 to 1.

2. The process of claim 1 wherein a temperature in the range of from about −70° C. to about −110° C. is employed.

3. The process of claim 1 wherein said methylating agent is methyl iodide and said base is sodium hydride.

4. The process of claim 1 wherein m is 1; $R^2$ is acetoxy, tertbutoxy, methoxymethoxy, benzyloxy or tetrahydropyranyloxy; $R^3$ is a hydrogen atom or a methyl or ethynyl group; or $R^2$ and $R^3$ taken together are lower alkylenedioxy or phenylenedioxy; $R^4$ is a hydrogen atom; $R^5$ is a lower alkylenedioxy or lower alkanoylox group; and $R^6$ and $R^7$ each is a hydrogen atom.

5. The proces of claim 4 wherein $R^1$ is 3-(lower alkylene-dioxy)butyl.

6. The process of claim 4 wherein $R^1$ is 3,3-orthophenylenedioxybutyl.

7. The process of claim 4 wherein $R^1$ is 3-oxobutyl.

8. The process of claim 4 wherein $R^1$ is (3,5-dimethyl-4-isoxazolyl)methyl.

* * * * *